(12) United States Patent
Voyeux et al.

(10) Patent No.: US 9,804,064 B2
(45) Date of Patent: Oct. 31, 2017

(54) POSITIVE DISPLACEMENT PIPETTE HAVING AN IMPROVED EJECTION FUNCTION

(71) Applicant: Gilson SAS, Villiers le Bel (FR)

(72) Inventors: Claude Voyeux, Goussainville (FR); Thierry Thebaud, Senlis (FR)

(73) Assignee: GILSON SAS, Villiers le Bel (FR)

( * ) Notice: Subject to any disclaimer, the term of this patent is extended or adjusted under 35 U.S.C. 154(b) by 218 days.

(21) Appl. No.: 14/345,294

(22) PCT Filed: Sep. 18, 2012

(86) PCT No.: PCT/EP2012/068294
§ 371 (c)(1),
(2) Date: Mar. 17, 2014

(87) PCT Pub. No.: WO2013/041505
PCT Pub. Date: Mar. 28, 2013

(65) Prior Publication Data
US 2014/0298925 A1  Oct. 9, 2014

(30) Foreign Application Priority Data
Sep. 19, 2011 (FR) ...................................... 11 58309

(51) Int. Cl.
*G01N 1/14* (2006.01)
*B01L 3/02* (2006.01)

(52) U.S. Cl.
CPC ............... *G01N 1/14* (2013.01); *B01L 3/022* (2013.01); *B01L 3/0217* (2013.01); *B01L 3/0279* (2013.01); *B01L 2200/02* (2013.01)

(58) Field of Classification Search
USPC .......................................... 73/864.14–864.16
See application file for complete search history.

(56) References Cited

U.S. PATENT DOCUMENTS

| | | |
|---|---|---|
| 3,525,264 A | 8/1970 | Nieglos et al. |
| 4,050,316 A | 9/1977 | Rapoza |

(Continued)

FOREIGN PATENT DOCUMENTS

| | | |
|---|---|---|
| DE | 2647883 | 5/1977 |
| DE | 10 2008 058 067 A1 | 5/2010 |

(Continued)

OTHER PUBLICATIONS

English language translation of the International Preliminary Examination Report issued in PCT/EP2012/068294, Sep. 10, 2013.

(Continued)

*Primary Examiner* — Paul West
*Assistant Examiner* — Mark A Shabman
(74) *Attorney, Agent, or Firm* — Miles & Stockbridge P.C.

(57) ABSTRACT

A positive displacement sampling pipette which includes a control rod, the bottom end of which controls the displacement of a device for gripping the top end of a piston of a capillary-piston assembly intended to cooperate with said pipette. The pipette includes an ejection rod of the capillary-piston assembly, movably mounted with respect to the control rod such that its bottom end exerts an ejection strain on the top end of the piston accommodated in the gripping device during a relative displacement between the ejection rod and the control rod.

14 Claims, 4 Drawing Sheets

(56) References Cited

U.S. PATENT DOCUMENTS

| | | | |
|---|---|---|---|
| 4,099,548 A | 7/1978 | Sturm et al. | |
| 4,154,108 A | 5/1979 | Vollinger et al. | |
| 4,362,064 A | 12/1982 | D Autry | |
| 4,567,780 A * | 2/1986 | Oppenlander | B01L 3/0224 422/525 |
| 4,616,514 A | 10/1986 | Magnussen et al. | |
| 5,021,217 A | 6/1991 | Oshikubo | |
| 5,413,006 A * | 5/1995 | D'Autry | B01L 3/0224 422/925 |
| 7,320,260 B2 * | 1/2008 | Belgardt | B01L 3/0217 73/864.14 |
| 2005/0155438 A1 | 7/2005 | Belgardt | |
| 2014/0298925 A1 | 10/2014 | Voyeux et al. | |
| 2016/0051978 A1 | 2/2016 | Voyeux et al. | |

FOREIGN PATENT DOCUMENTS

| | | |
|---|---|---|
| EP | 0014120 A1 | 8/1980 |
| EP | 032469 | 7/1981 |
| EP | 0078724 A1 | 5/1983 |
| FR | 2446672 A1 | 8/1980 |
| FR | 2980123 A1 | 3/2013 |
| JP | 4225845 | 8/1992 |

OTHER PUBLICATIONS

International Search Report and Written Opinion issued in PCT/EP2012/068294, dated Dec. 11, 2012.
International Preliminary Examination Report issued in PCT/EP2012/068294, dated Sep. 10, 2013.
Preliminary French Search Report for FR 1360906 (dated Jul. 30, 2014).
International Search Report for PCT/EP2014/073631 (dated Jan. 8, 2015).
International Search Report dated May 8, 2014 for International Application No. PCT/EP2014/055769.
French Search Reporting dated Feb. 3, 2014 for French Application No. 1352660.
Non-Final Office Action dated Jun. 29, 2017 for related U.S. Appl. No. 14/779,518.
Non-Final Office Action dated Jun. 30, 2017 for related U.S. Appl. No. 15/034,833.

* cited by examiner

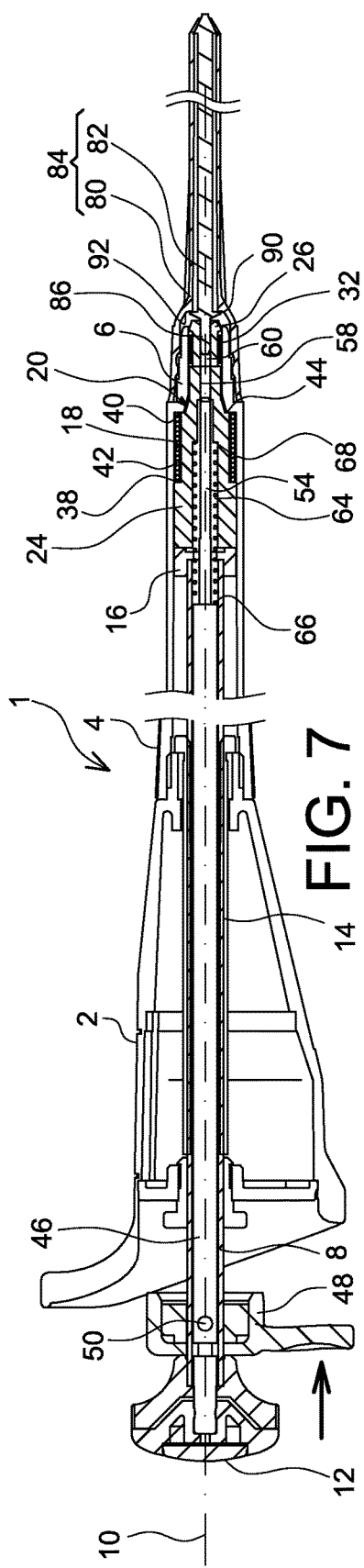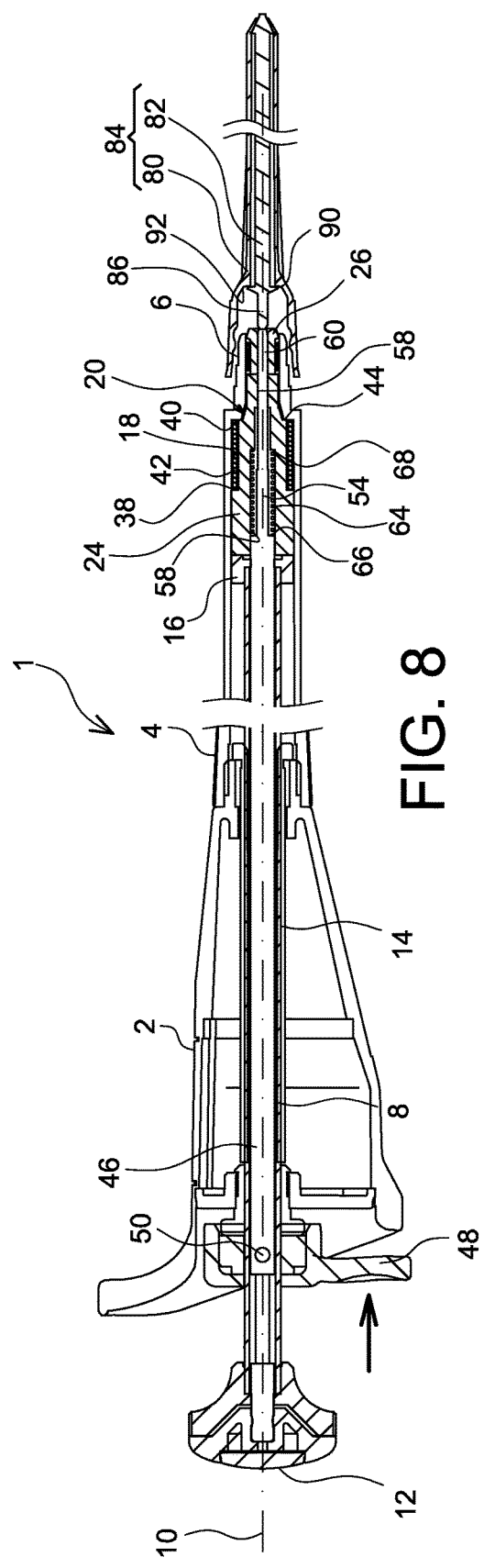

POSITIVE DISPLACEMENT PIPETTE HAVING AN IMPROVED EJECTION FUNCTION

CROSS-REFERENCE TO RELATED APPLICATIONS

This application is a National Stage Entry under 35 U.S.C. §371 of International Application No. PCT/EP2012/068294, filed Sep. 18, 2012, which claims the benefit of FR Patent Application No. 1158309, filed Sep. 19, 2011, the contents of which are herein incorporated by reference.

TECHNICAL FIELD

The present invention relates to the field of positive displacement sampling pipettes.

Such pipettes are intended to cooperate with capillary-piston type items, the piston of which is provided to be directly in contact with the sample to be sampled, before being ejected or reused. The positive displacement pipettes thus have a design different from that of more conventional air displacement pipette, wherein the piston is an integral part of the pipette.

The invention more specifically relates to the ejection function of the capillary-piston assembly.

STATE OF PRIOR ART

Positive displacement pipettes are usually used for sampling viscous, volatile liquids and/or contaminants. Their association with "capillary-piston" type items prevents the pipette from being contaminated.

Such a pipette is for example known from document FR 2 446 672.

On positive displacement pipettes known from prior art, a control rod is provided the bottom end of which controls the displacement of a device for gripping the top end of a piston, belonging to a capillary-piston assembly intended to cooperate with the pipette. This gripping device is also known as "clip".

The pipette is designed such as to be able to exert two successive strokes downwardly with the control rod, via a control button arranged at its top end. The first stroke of the control rod corresponds to the stroke for dispensing the sampled sample. It is performed by opposing to the return force of a first spring, preferably a compression spring. The second stroke of the control rod corresponds to the presentation and opening of the piston gripping clip. It is performed by opposing to the return force of a second spring, preferably a compression spring, arranged along the same direction as the first spring and having a much higher stiffness.

More precisely, this second stroke results in extracting the clip jaws from a sheath encircling them. Once the jaws are released from their sheath, they can readily let the top end of the piston enter upon installing the item onto the pipette, with on the other hand the simultaneous fitting of the capillary on the tip thereof.

The first raising phase of the control rod, under the effect of the return force of the second spring, results in retracting the jaws into the clip sheath, with the top end of the piston being kept by the jaws in clamped position. The second raising phase of the control rod, under the effect of the return force of the first spring having a lower stiffness, results in the displacement of this rod as well as the clip encircling the piston up to a high position, with respect to the pipette body.

To perform a sample sampling, the operator should again perform the first stroke of the control rod with the piston embedded, up to the total compression of the first spring bringing the piston to its low sampling point. Continuing the stroke at this stage, that is an accidental triggering of the second stroke against the second spring, would result in an excessive displacement of the piston downwardly, and would lead to an error in the amount of sampled sample. An excessive overstroke of the piston could even lead to the accidental ejection of the piston and capillary, because of the release of the clip jaws by the sheath which surrounds them, and due to the jaws bearing against the capillary. Such an ejection is not only a problem in terms of productivity, but also generates non-negligible risks of liquid projection when the capillary-piston assembly falls into a liquid container.

When the piston has reached its low point at the end of the first stroke, the item is dipped into the liquid to be sampled. To ensure sampling, the operator then gradually releases the pressure exerted by his/her thumb onto the control button, which enables the control rod and the piston to be raised under the effect of the return force of the first spring. During this raising, the liquid in contact with the low end of the piston enters the capillary.

For dispensing, the operator performs again the first stroke of the control rod by pressing his/her thumb unto the control button, by placing the capillary into the container intended to receive the liquid. Here again, in case of a piston overstroke, the latter might be accidentally ejected with the capillary, thus generating again a risk of liquid accidental projection.

Finally, once the liquid dispensing operation is completed, the operator can perform the second stroke of the control rod in order to cause the desired ejection of the capillary-piston item. However, this ejection operation is performed using only the thumb of the operator by counteracting the return force of the second spring, which is necessarily substantial in order to contrast with the return force of the first spring, and thus be able to ensure its delivery function of a sensitive signal to the operator at the end of the first stroke. The high stiffness of the second spring thus makes the pipette perfectible from the ergonomic point of view, especially as this drawback also occurs during the abovementioned clip opening operation, before introducing the piston.

DISCLOSURE OF THE INVENTION

One object of the invention is therefore to at least partially overcome the abovementioned drawbacks, relating to embodiments of prior art.

To do this, one object of the invention is to provide a positive displacement sampling pipette, comprising a control rod the bottom end of which controls the displacement of a device for gripping the top end of a piston belonging to a capillary-piston assembly for cooperating with said pipette, the latter including also a rod for ejecting said capillary-piston assembly, movably mounted with respect to said control rod such that its bottom end can exert an ejection strain on the top end of said piston accommodated in said gripping device, during a relative displacement between the ejection rod and the control rod.

The invention is remarkable in that it is based on a design dissociating elements enabling the control function of the pipette and the ejection function of the capillary-piston item to be ensured.

More precisely, the invention provides for the item ejection to be performed by a dedicated rod, distinct from the control rod. Consequently, unlike embodiments of prior art, the risks of item accidental ejection by the control rod are advantageously reduced to zero. Thus, during the manipulation of the pipette according to the invention, the operator can actuate the control rod without worrying about the risks of such a loss, which overall enables the ergonomy, sampling reproducibility and productivity to be improved.

These improvements are even further enhanced by the ejection technology employed, which is based on the piston thrust using the bottom end of the ejection rod, in turn driving the capillary in its stroke, by means of a stop. The force to be delivered to ensure the item ejection can thus be much lower than that previously required to counteract the return force of the spring having a high stiffness, because it is no longer necessary to provide for a high differential of spring stiffnesses to produce a sensory signal for the operator. Moreover, the low bearing force required to disengage the piston from the gripping device and remove the capillary from the pipette tip has no incidence on the accidental loss risks of the capillary-piston item, as has been explained above.

Preferably, said gripping device has the form of a clip with at least two jaws returned into a clamped position by elastic return means, preferably surrounding these same jaws. This enables the pipette manipulation process to be simplified, in particular as regards the item installation on the same.

In this regard, one object of the invention is also to provide a pipetting method using a positive displacement sampling pipette, comprising the following successive steps:

(a) fitting the capillary of the capillary-piston assembly onto a tip of the pipette, and introducing the top end of the piston of the assembly into the clip during the displacement of said control rod up to a low position, said introducing being performed by moving apart the radially outwardly biased jaws by the bearing of the top end of the piston, said moving apart being allowed by deforming said elastic return means associated with said jaws;

(b) sampling and dispensing a sample by actuating said control rod;

(c) ejecting the capillary-piston assembly by actuating said ejection rod.

During step (a), the fitting of the capillary and the introduction of the piston are preferentially successively performed. Thus, the fitting operation is carried out in an analogous way to that performed with conventional air displacement pipettes, without actuating the control rod. When the fitting of the capillary is completed, the piston introduction into the clip is thus initiated and performed by simply displacing the control rod, by virtue of an action only requiring a small effort from the operator, substantially conditioned by the stiffness of the elastic return means surrounding the jaws. The above operations are thus usual for operators, which enhances the pipette ergonomy and provides gains in terms of productivity.

It is noted that according to an alternative, during step (a), the fitting of the capillary and the introduction of the piston can be simultaneously performed, without departing from the scope of the invention.

At the end of step (a), the piston is in a stop low position in the capillary. Thus, to simplify the sampling process, said control rod is kept in a low position at the end of step (a) until the sample is sampled, during which the control rod raises with the piston to cause the liquid suction.

Preferably, said ejection rod is accommodated inside the hollow control rod, even if it could be different, without departing from the scope of the invention. By way of indicative example, the ejection rod could be accommodated within the external pipette body, around the control rod, and having a low end entering inside the gripping device to be able to apply the ejection effort specific to the present invention, onto the top end of the piston.

Preferably, the pipette includes a control button arranged at the top end of the control rod, as well as an ejection button arranged at the top end of the ejection rod. Said ejection button is thus preferentially arranged between the control button and a handle forming pipette body.

Preferably, said ejection button is carried by a support member mounted on the ejection rod and passing through an oblong passageway provided in the control rod, said support member being able to slide in said oblong passageway.

Preferably, said pipette is equipped with elastic return means returning said ejection rod into a high position relative to said control rod. This is preferentially a compression spring.

Preferably, said elastic return means returning said ejection rod in a high position relative to said control rod are designed such that upon actuating said ejection button, a first stroke results in driving said control rod with said ejection rod, via said elastic return means, and a second stroke is triggered when the displacement of the control rod is translationally stopped by means of a stop at the end of said first stroke, said second stroke resulting in said relative displacement between the ejection rod and the control rod, causing said ejection strain on the top end of said piston.

Preferably, the pipette is designed such that at the end of said first stroke, said control rod being stopped places said gripping device at least partially projecting downwardly from a pipette tip on which the capillary of said capillary-piston assembly is intended to be fitted. This enables in particular the clip jaws to be easily moved apart, upon introducing the top end of the piston.

Preferably, the bottom stop for said control rod is arranged on a low part of a pipette integrating the tip, and preferably designed to cooperate with a stop provided on said gripping device interposed between said control rod and the bottom stop. Alternatively, the control rod could be equipped with a stop enabling it to directly bear against the stop of the low part of the pipette, without departing from the scope of the invention.

Finally, it is noted that the pipette could be of a single volume sampling type, or include a device for adjusting the sample volume to be sampled.

Further advantages and characteristics of the invention will appear in the non-limiting detailed description below.

BRIEF DESCRIPTION OF THE DRAWINGS

This description will be made with regard to the appended drawings wherein:

FIGS. 5 to 8 represent different views schematically representing the operation of the pipette shown in the preceding figures.

DETAILED DISCLOSURE OF PREFERRED EMBODIMENTS

Figure 1:
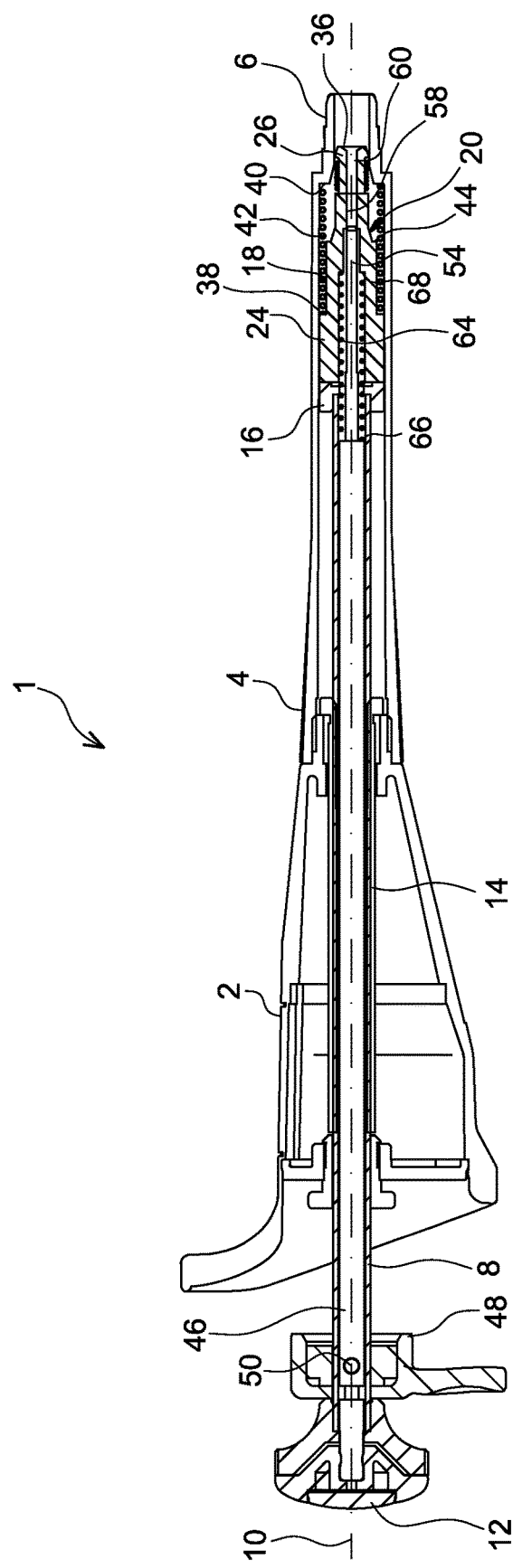
FIG. 1 represents a longitudinal cross-section view of a positive displacement sampling pipette, according to a preferred embodiment of the present invention.

First, in reference to FIG. 1, a positive displacement sampling pipette 1 is represented according to a preferred embodiment of the present invention.

Throughout the description that follows, the terms "top" and "bottom" are to be considered with the pipette kept vertically, in a pipetting position or close to this same position.

The pipette 1 has an outer body the top part of which forms a handle 2 for the operator, and the bottom part 4 of which is more tapered, ending downwardly with a tip 6 on which a capillary is intended to be fitted. The bottom part 4 is preferentially mounted screwed on the handle forming body 2, so as to facilitate assembly/disassembly.

Figure 2:
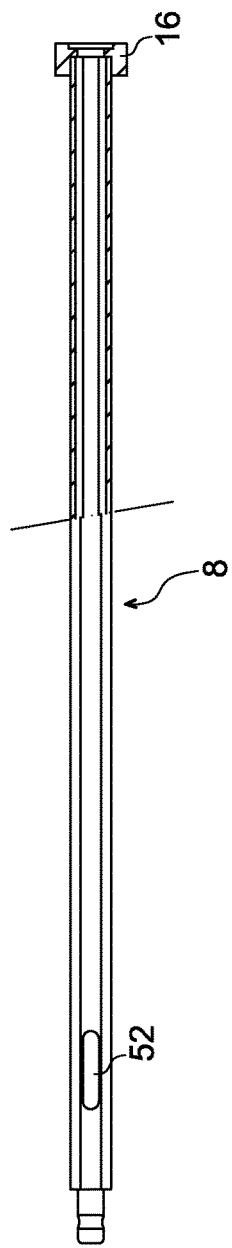
FIG. 2 represents a front view of the control rod equipping the pipette shown in the preceding figure.

The pipette integrates a control rod 8, slidably accommodated inside the pipette outer body. The rod 8 is hollow, and arranged along the longitudinal axis 10 of the pipette. Its top end projects upwardly from the handle forming body 2, and carries a control button 12 intended to be actuated by an operator's thumb holding the body 2 with one of his/her hands. As is shown in FIG. 2, the rod has a non-circular shaped transverse cross-section, herein a hexagonal or orthogonal shape. It is slidably accommodated through a screw 14 for adjusting the volume to be sampled, the inner hollow part of which is of a complementary form to the outer surface of the rod 8, and the outer surface of which is threaded, screwedly mounted to the lower end of the handle forming body 2.

In a known manner, the rotation of the control rod 8 by its button 12 enables the adjusting screw to be displaced relative to the pipette outer body along the direction of the axis 10, and thus results in a change in a sample volume intended to be sampled.

The bottom end of the control rod 8, acting as a guide in the bore 18 provided within the low part 4, is axially bearing against a clip 20 also slidably mounted in the bore 18.

Figure 4:
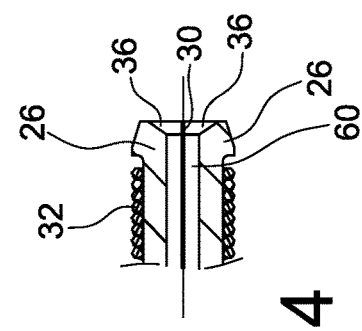
FIG. 4 represents a longitudinal cross-section partial view of the clip shown in the preceding figure.
Figure 3:
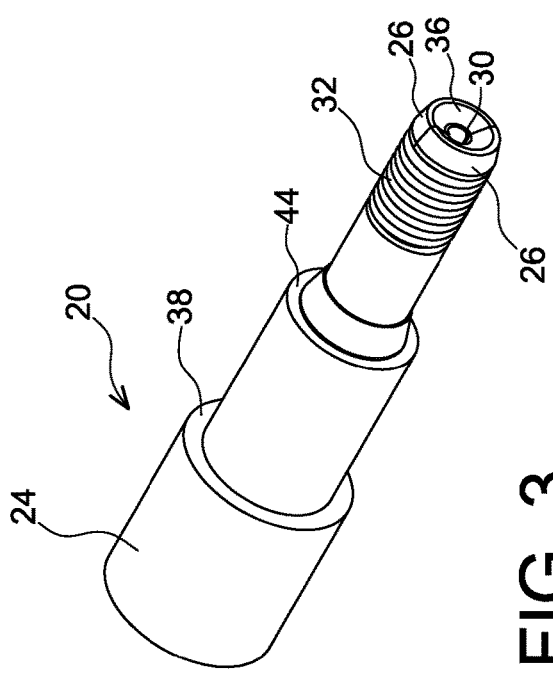
FIG. 3 represents a perspective view of the piston clip equipping the pipette shown in FIG. 1.
Figure 5:
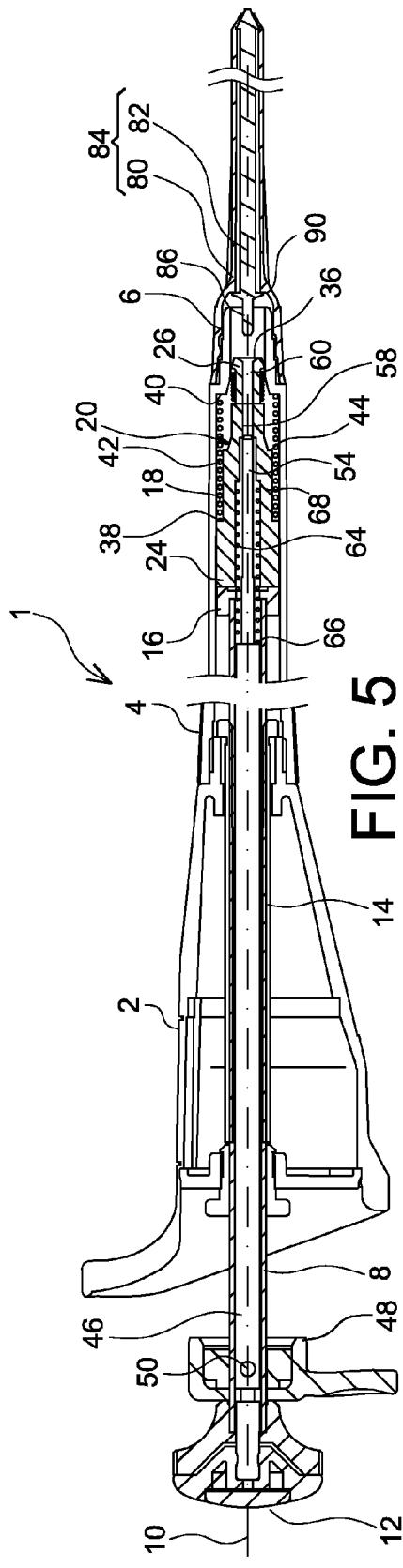

As can be seen in FIGS. 1, 2 and 4, the clip 20 includes a body 24 for contacting the bottom end 16 of the control rod, extended downwardly by two or more jaws. By way of indicative example, two jaws 26 are provided, one made as a single piece with the clip body 24, and the other mounted to this same clip body. Elastic return means enable both jaws to be returned into a clamped position, wherein they are radially inwardly retracted. The slip 30 separating them then has a low dimension.

To do this, the elastic return means bias the jaws 26 radially inwardly, preferably by surrounding the same jaws. This can thus be a spring 32 having a general annular shape, the diameter of which can be increased when it is radially outwardly stressed. In the example shown in the figures, the spring 32 takes the shape of a spiral spring encircling the external surface of the jaws 26.

As can be better seen in FIG. 4, each jaw 26 has a chamfered end 36 so as to facilitate insertion of the piston, as will be explained hereinafter.

Furthermore, the clip body 24 has a first shoulder 38 directed downwardly, facing away a shoulder 40 provided on the bottom part 4, in proximity of the tip 6. A return spring 42 is accommodated bearing between these two shoulders 38, 40, in order to make up a return spring at the high position of this clip 20 and of the control rod bearing against it, extending therefrom. The return force developed by this compression spring 42 effectively causes the control rod 8 to assume its high position with respect to the outer body, a conventional high stop (not shown) being provided to that end on this same outer body.

The clip 20 includes a second shoulder 44, also directed downwardly facing away the shoulder 40. The second shoulder 44 is located lower and radially inwardly with respect to the first shoulder 38. It is thus surrounded by the spring 42. As will be described hereinafter, it is provided to make up a low stop for the clip 20 and the control rod 8 bearing against this same clip. In the high position shown in FIG. 1, the ends 36 of the clip jaws are located in the tip 6, in a retracted position inside the same. The inside diameter of the tip has on the other hand a value close to the average diameter of the clip 20 with its jaws 26 in a clamped position.

One of the features of the present invention lies in the presence of an ejection rod 46 slidably mounted inside the hollow control rod 8. This ejection rod 46 has an external surface complementary to the internal surface of the control rod 8. Its top end is arranged between the control button 12 and the handle forming body 2, and carries an ejection button 48. To do this, the button 48 is carried by a support member 50 having a pin shape, which is mounted to the ejection rod 8 and which passes through an oblong passageway 52 provided in the control rod, shown in FIG. 2. The pin 50 is then able to slide in the oblong passageway 52 during the relative displacement between both rods 8, 46, corresponding to a sliding along the direction of the axis 10.

The bottom end 54 of the ejection rod 46 is more tapered, having a cylindrical shape and circular cross-section. It enters within a bore 58 provided within the hollow body, passing through up the space 60 defined between the clips.

At the shape change between the bottom end 54 and the high part of the rod 46, this defines a shoulder 66 directed downwardly, facing away a shoulder 68 provided on the clip 20, in the bore 58. A return spring 64 is accommodated bearing between these two shoulders 66, 68, in order to make up a return spring in a high position for the ejection rod 46 with respect to the control rod 8 located outwardly. The return force developed by this compression spring 64 effectively causes the ejection rod 46 to assume its high position with respect to the control rod 8, a high stop being made by pressing the ejection button surrounding the rod 8, on the bottom end of the control button 12, as can be seen in FIG. 1. Such a stop could alternatively being made by pressing the pin 50 onto the top end of the oblong passageway 52 provided transversely on the control rod.

In reference now to FIGS. 5 to 8, the operation of the pipette 1 will be described.

First, the operator gripping the pipette through the handle 2 engages the tip 6 in a capillary 80 of a capillary-piston item assembly 84, preferably arranged in a case, also called "rack". By exerting a vertical pressure downwardly onto the pipette, he/she achieves the fitting of the capillary 80 on the tip 6, much like fitting a capillary or a conventional cone onto the tip of a conventional air displacement pipette. This sleeving has been schematically represented in FIG. 5.

Figure 6:
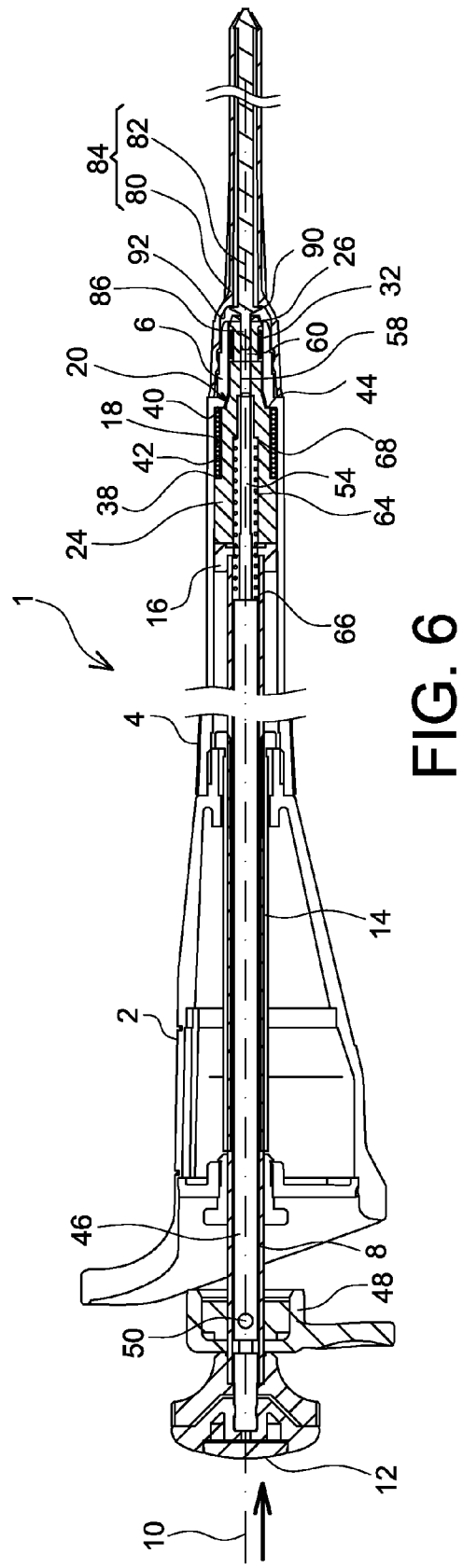

Then, as can be seen in FIG. 6, the operator presses the control button 12 in order to bring the control rod and the clip into a low position. The object of this displacement is to lead to the introduction of the top end 86 of the piston 82 of the assembly 84 into the clip 24. This piston introduction will be detailed below.

During a descent of the rod 8 counteracting the return force of the spring 42, the chamfered ends 36 of the clip jaws start with contacting the end 86 of the piston 82, that they push accordingly into a low position in the capillary 80 if not already made. This low position is reached when the flange 90 located under the top end 86 of the piston 82 abuts against a corresponding shoulder 92 inside the capillary 80.

Then, as the descent goes on, the jaws 36 are radially outwardly biased by the top end of the piston 86 bearing against the chamfered ends 36 of these jaws. This results in the jaws being moved apart, which is allowed by the stressing of the spiral spring 32 surrounding these jaws, and permitted by a sufficient bore diameter in the tip 6. Besides, during this descent, a low part of the jaws is intended to project from the tip 6 so as to enable these jaws to be more radially outwardly deformed.

When the jaws move apart and the descent of the control rod proceeds, this leads to gradually introduce the top end 86 of the piston into the space 60 defined by these jaws. The introduction is completed when the ends 36 of the jaws abut against the flange 90 of the piston, in turn abutting against the shoulder 92, as is shown in FIG. 6. This position corresponds above all to the low position of the control rod and of the clip bearing against this rod, since the clip 20 is then in a low stop on the lower body 4, by contact between the shoulders 44, 40. At this stage, the spring 42 is compressed to the maximum between both shoulders 38, 40.

At the end of this step, the piston is located at the low stop position in the capillary. Thus, to simplify the sampling process, the control rod 8 is kept in a low position until the sample is sampled, during which the control rod raises with the piston to cause the liquid suction.

The dispensing of the liquid sample is then performed, by displacing the control rod via its button 12, in an identical way as that performed for gripping the piston. Indeed, the stroke is the same, bringing the control rod 8 into a low position up to the contact between the shoulders 44, 40, shown in FIG. 6.

Finally, the ejection of the item assembly 84 is carried out, using the ejection rod 46 actuated by its control button 48.

The stiffness of the return spring 64 is such that during a first stroke, this spring is not compressed and the ejection rod 46 being displaced drives the control rod 8 with it. This phase has been schematically represented in FIG. 7.

When the control rod 8 is displaced and the clip 20 is translationally stopped by means of a stop of the shoulders 44, 40 and that the button 48 continues to be actuated downwardly, then a second stroke of the ejection rod occurs, during which there is a relative displacement of the rod 46 with respect to the rod 8 staying fixed. This results in bringing the bottom end 54 of the rod 46 in contact with the top end 86 of the piston 82, and then in exerting an ejection effort on this same top end of said piston. The rod 46 thus drives off the piston 82 which, by bearing via its flange 90, drives the capillary 80 with it until the item assembly 84 is ejected, as has been schematically represented in FIG. 8. In this regard, the shape of the end 54 of the ejection rod 46 can be optimized to best fit snugly the top end 86 of the piston 82, so as to promote contact between both pieces, by centring.

Of course, various changes can be made by those skilled in the art to the invention just described, only by way of non-limiting examples.

The invention claimed is:

1. A positive displacement sampling pipette, comprising:
    a control rod having a bottom end which controls a displacement of a device for gripping a top end of a piston belonging to a capillary-piston assembly adapted to cooperate with said pipette,
    wherein said pipette includes an ejection rod for ejecting said capillary-piston assembly, and
    wherein said ejection rod is movably disposed within said control rod such that a bottom end of the ejection rod exerts an ejection strain on the top end of said piston accommodated in said gripping device during a relative displacement between the ejection rod and the control rod.

2. The pipette according to claim 1, wherein the control rod is hollow and said ejection rod is accommodated inside the hollow control rod.

3. The pipette according to claim 2, further comprising a control button arranged at the top end of the control rod, as well as an ejection button arranged at the top end of the ejection rod.

4. The pipette according to claim 3, wherein the ejection button is arranged between the control button and a handle forming a pipette body.

5. The pipette according to claim 4, wherein said ejection button is carried by a support member mounted on the ejection rod and passing through an oblong passageway provided in the control rod, said support member being able to slide in said oblong passageway.

6. The pipette according to claim 1, wherein the gripping device has a form of a clip having at least two jaws biased into a clamped position by elastic return means.

7. The pipette according to claim 6, wherein the elastic return means associated with the at least two jaws surround the at least two jaws.

8. The pipette according to claim 1, further comprising elastic return means biased to retain said ejection rod into a high position relative to said control rod.

9. The pipette according to claim 8, further comprising:
    a control button arranged at the top end of the control rod, as well as an ejection button arranged at the top end of the ejection rod,
    wherein said elastic return means which bias said ejection rod into the high position relative to said control rod are designed such that upon actuating said ejection button, a first stroke results in driving said control rod with said ejection rod, via said elastic return means, and
    wherein a second stroke is triggered when the displacement of the control rod is translationally stopped by means of a stop at the end of said first stroke, said second stroke resulting in said relative displacement between the ejection rod and the control rod, thus causing said ejection strain on the top end of said piston.

10. The pipette according to claim 9, wherein at an end of said first stroke, said control rod is stopped to place said gripping device at least partially projecting downwardly from a pipette tip on which the capillary of said capillary-piston assembly is adapted to be fitted.

11. The pipette according to claim 10, wherein a bottom stop for said control rod is arranged on a low part of a pipette integrating the tip, and cooperates with a stop provided on said gripping device interposed between said control rod and the bottom stop.

12. The pipette according to claim 1, further comprising a device for adjusting a sample volume to be sampled.

13. A pipetting method using a positive displacement sampling pipette including
    a control rod having a bottom end which controls a displacement of a device for gripping a top end of a piston belonging to a capillary-piston assembly adapted to cooperate with said pipette, the pipette including an ejection rod for ejecting said capillary-piston assembly, said ejection rod being movably disposed within said control rod such that a bottom end of the ejection rod exerts an ejection strain on the top end of said piston accommodated in said gripping device during a relative displacement between the ejection rod and the control rod, and the gripping device having a form of a clip having at least two radially outwardly-biased jaws biased into a clamped position by elastic return means, the pipetting method comprising the following successive steps:

(a) fitting a capillary of the capillary-piston assembly onto a tip of the pipette, and introducing the top end of the piston of the assembly into the clip during the displacement of said control rod into a low position, said introducing being performed by moving apart the at least two radially outwardly biased jaws by bearing the top end of the piston, said moving apart being allowed by deforming said elastic return means associated with said at least two radially outwardly biased jaws;

(b) sampling and dispensing a sample by actuating said control rod; and (c) ejecting the capillary-piston assembly by actuating said ejection rod.

14. The method according to claim 13, further comprising at the end of step (a), keeping said control rod in the low position until the sample is sampled.

\* \* \* \* \*